(12) United States Patent
Zaldivar et al.

(10) Patent No.: US 12,320,765 B2
(45) Date of Patent: Jun. 3, 2025

(54) QUALITY CONTROL EVALUATION METHOD OF CYANATE ESTER MATRIX RESIN MATERIAL WITHIN CFRP COMPOSITE CONCERNING LOCALIZED HYDROLYTIC DEGRADATION

(71) Applicant: The Aerospace Corporation, El Segundo, CA (US)

(72) Inventors: Rafael J. Zaldivar, Redondo Beach, CA (US); Hyun I. Kim, Brea, CA (US); Geena L. Ferrelli, Marina Del Rey, CA (US)

(73) Assignee: THE AEROSPACE CORPORATION, Segundo, CA (US)

( * ) Notice: Subject to any disclaimer, the term of this patent is extended or adjusted under 35 U.S.C. 154(b) by 450 days.

(21) Appl. No.: 18/061,908

(22) Filed: Dec. 5, 2022

(65) Prior Publication Data
US 2024/0183805 A1    Jun. 6, 2024

(51) Int. Cl.
| | |
|---|---|
| *G01N 23/2251* | (2018.01) |
| *G01N 1/32* | (2006.01) |
| *G01N 33/44* | (2006.01) |
| *G01Q 60/24* | (2010.01) |

(52) U.S. Cl.
CPC .......... *G01N 23/2251* (2013.01); *G01N 1/32* (2013.01); *G01N 33/442* (2013.01); *G01Q 60/24* (2013.01); *G01N 2223/07* (2013.01); *G01N 2223/418* (2013.01); *G01N 2223/507* (2013.01)

(58) Field of Classification Search
USPC ....................................................... 250/307
See application file for complete search history.

(56) References Cited

U.S. PATENT DOCUMENTS

| | | | |
|---|---|---|---|
| 9,352,858 B2 | 5/2016 | Coleman et al. | |
| 2008/0075954 A1* | 3/2008 | Wardle | C01B 32/18 |
| | | | 156/60 |
| 2009/0311166 A1* | 12/2009 | Hart | B82B 1/00 |
| | | | 977/773 |

OTHER PUBLICATIONS

Gul, Rizwan M., "The Effects of Peroxide Content on the Wear Behavior, Microstructure and Mechanical Properties of Peroxide Crosslinked Ultra-High Molecular Weight Polyethylene Used in Total Hip Replacement", J Mater Sci: Mater Met (2008) 19:2427-2435.
Zaldivar, et al., "Identification and Evaluation of Progressive Thermal Degradation Caused by Carbamate Formation in Cyanate Ester Resin-Based Composites", Polymer Engineering and Science, 2011.
Zaldivar, R.J., "Lessons Learned in the Processing of Polycyanurate Resin Composites", The Aerospace Corporation Report No. TR-98(8565)-8; Feb. 15, 2002.

* cited by examiner

*Primary Examiner* — Kiet T Nguyen
(74) *Attorney, Agent, or Firm* — LeonardPatel PC

(57) ABSTRACT

Evaluating the quality of cyanate ester matrix resin material includes inserting a small piece of a deposit extracted from a composite laminate into an epoxy for cross-sectional analysis, and performing cross-sectional polishing on the small piece of the deposit. Evaluating the quality of the cyanate ester matrix resin material also includes performing resolution imaging to study a plurality of plies in the small piece of the deposit to evaluate each ply without causing destruction to each of the plurality of plies.

20 Claims, 8 Drawing Sheets

Fig. 2
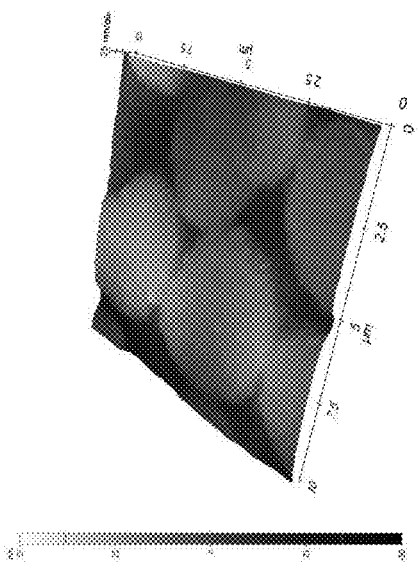
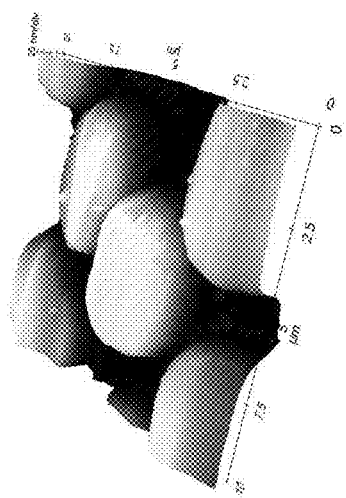
200(b)
200(a)
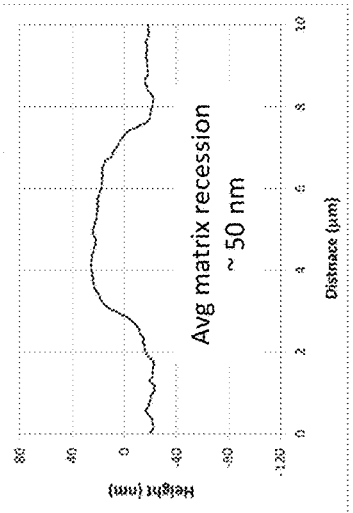
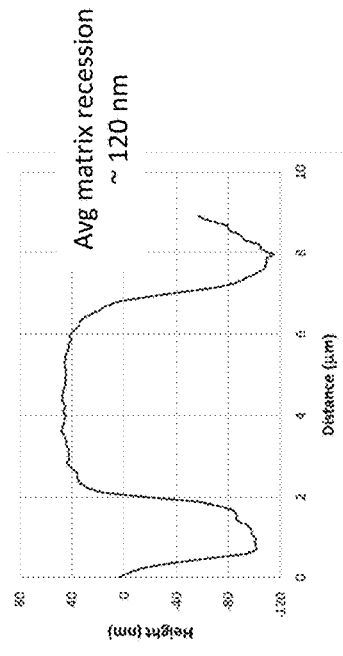
200

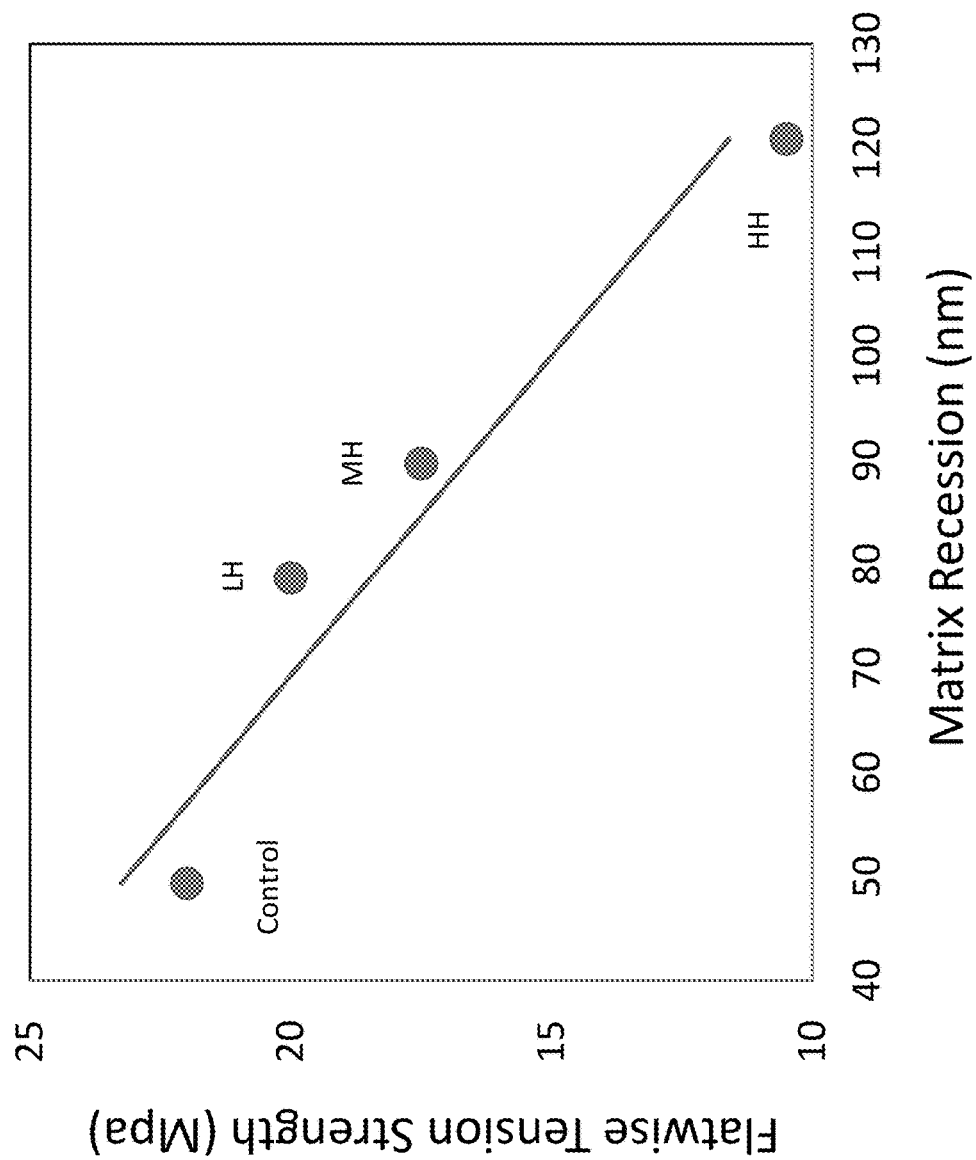

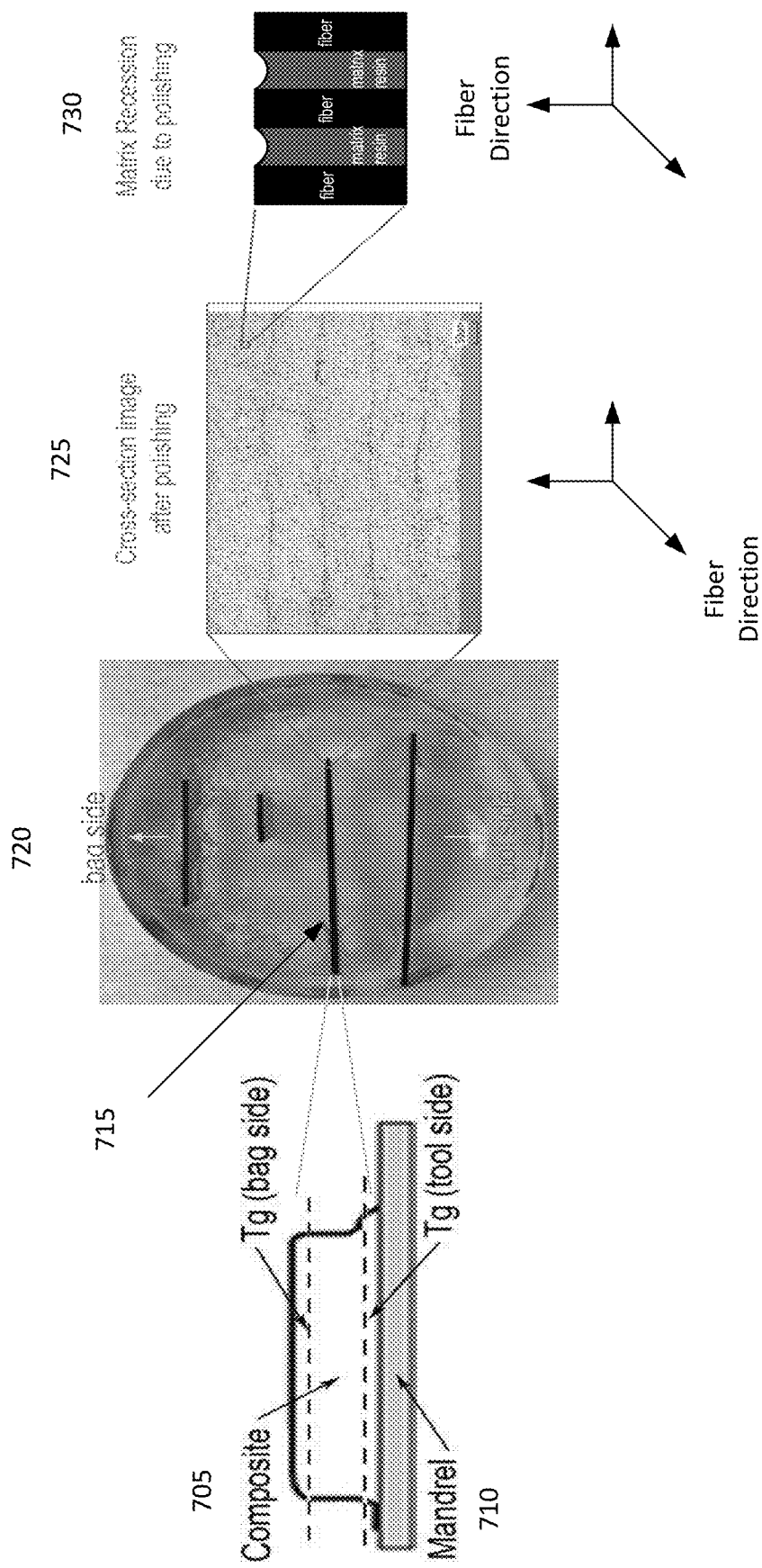

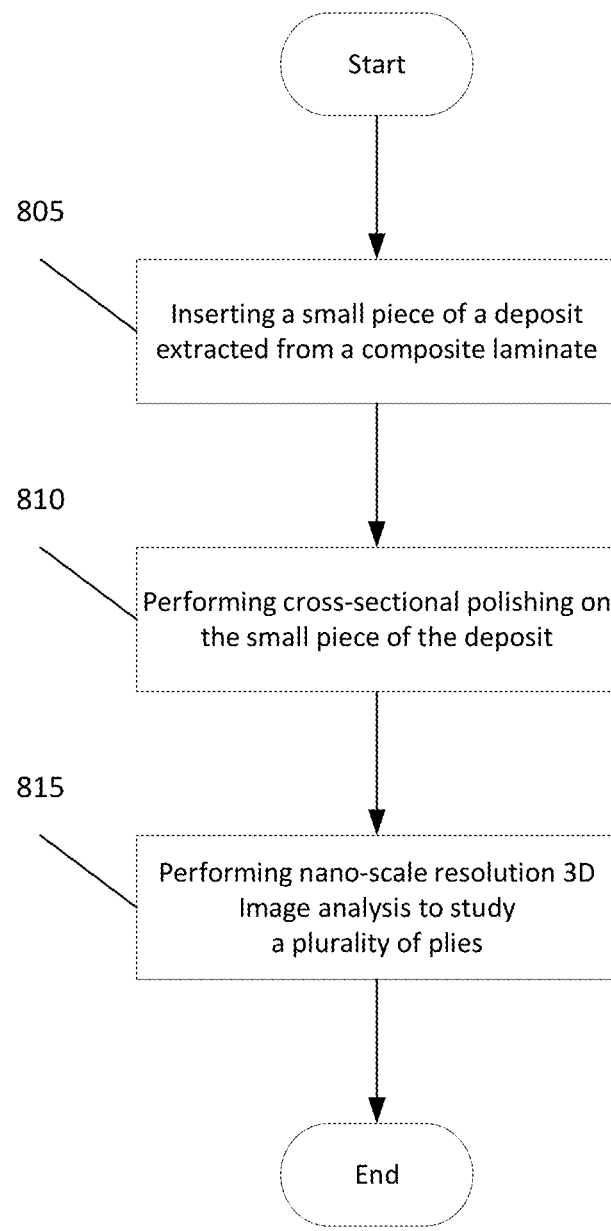

QUALITY CONTROL EVALUATION METHOD OF CYANATE ESTER MATRIX RESIN MATERIAL WITHIN CFRP COMPOSITE CONCERNING LOCALIZED HYDROLYTIC DEGRADATION

FIELD

The present invention relates to quality control evaluation technique, and more particularly, to a quality control method for evaluating a cyanate ester matrix resin material within CFRP composite concerning localized hydrolytic degradation.

BACKGROUND

There are a few analysis techniques available to identify material changes due to the introduction of moisture in a cyanate ester (CE) resin based composite during cure. The most useful conventional techniques involve measuring the glass transition temperature (Tg) measurement by dynamic mechanical analysis (DMA) or differential scanning calorimetry (DSC).

A challenge of performing DMA analysis to detect hydrolysis in a composite laminate arises from the highly localized nature of the phenomenon. The hydrolysis typically affects the outer 1~2 plies, which is just a small fraction of a nominal composite thickness. Consequently, a typical DMA measurement that analyzes through the entire thickness could yield a false negative because the signal from the unaffected plies would dominate over that from the unaffected plies. To obtain a more appropriate DMA measurement of the affected plies, all or most of the unaffected sections of the composite specimen must be removed, which can be difficult and time consuming. Furthermore, if the separation is not performed carefully, the plies of interest may be damaged and become unsuitable for DMA analysis.

DSC analysis can also be used to measure Tg by evaluating changes in heat capacity with temperature. However, this technique does not typically provide a very distinct value and the fibers in the composite themselves typically worsen the signal necessary for the identifying a Tg value. Also, the test usually provides one value for an entire specimen and mapping of the composite to understand the extent of this degradation is difficult to accomplish.

Accordingly, a new quality control evaluation technique with enhanced sensitivity may be beneficial.

SUMMARY

Certain embodiments of the present invention may provide solutions to the problems and needs in the art that have not yet been fully identified, appreciated, or solved by current quality control evaluation techniques. For example, some embodiments of the present invention pertain to quality control method for evaluating a CE matrix resin material within CFRP composite concerning localized hydrolytic degradation.

In one embodiment, a method for evaluating the quality of cyanate ester matrix resin material includes inserting a small piece of a deposit extracted from a composite laminate into an epoxy for cross-sectional analysis, and performing cross-sectional polishing on the small piece of the deposit. The method also includes performing resolution imaging to study a plurality of plies in the small piece of the deposit to evaluate each ply without causing destruction to each of the plurality of plies.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 2 is an image illustrating an example of an AFM scan and a line profile of the tool side of the control specimen versus that of the tool side for a specimen that has experienced hydrolysis and carbamate formation, according to an embodiment of the present invention.

FIG. 6 is a graph illustrating flatwise tension (FWT) strengths versus matrix recession (i.e., fiber height by AFM) for TC410/M55J laminates after cross-sectional polishing, according to an embodiment of the present invention.

FIG. 7 is a diagram illustrating a cross-section analysis of a composite laminate, according to an embodiment of the present invention.

FIG. 8 is a flow diagram illustrating a quality control evaluation method of a CE matrix resin material within a CFRP composite concerning localized hydrolytic degradation, according to an embodiment of the present invention.

DETAILED DESCRIPTION OF THE EMBODIMENTS

Figure 1:
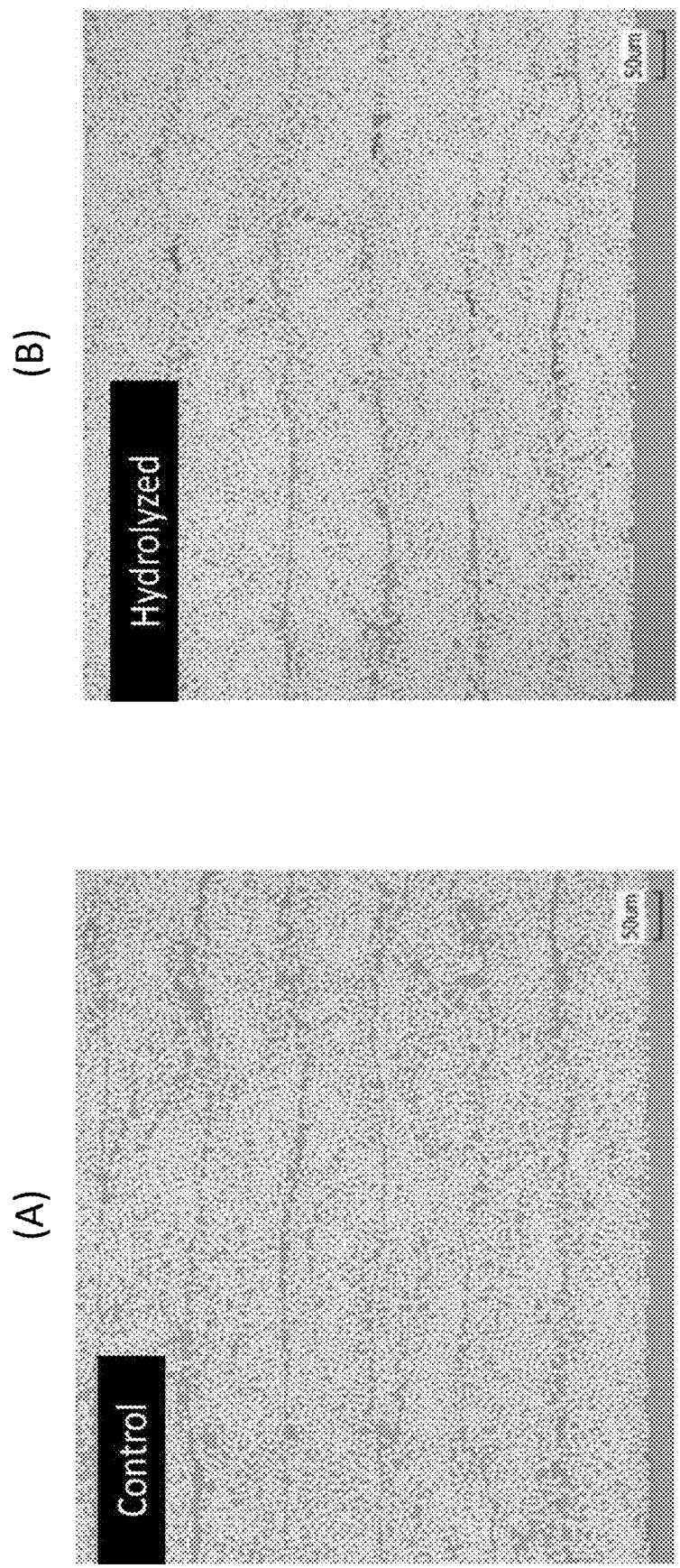
FIG. 1 is an image illustrating cross-section of laminate of TC410/M55J manufactured on a control (a) metal mandrel versus (b) a composite mandrel with pre-exposure to humidity to induce hydrolysis in the laminate during cure according to an embodiment of the present invention.

Cyanate ester (CE) resin-based composites continue to evolve into becoming the next generation of advanced structural materials for high-precision space applications. These resin composites have virtually replaced graphite/epoxy composites for these applications due to their very low moisture uptake (0.25-0.5%), low CTE, increased radiation resistance, and excellent mechanical performance. These improvements translate into increased dimensional stability for current and future advanced optical payloads over a wide range of possible environments.

However, a critical processing complication arising from "moisture sensitivity during cure" has been shown to result in severe manufacturing and bonding failures leading to costly schedule delays. Though impervious to water after cure, relatively small amounts of water during cure may severely affect the polymerization behavior of the matrix material leading to significant impacts on mechanical and thermal degradation. The water source may be at very low concentrations emanating from the environment or transferred as residual quantities of moisture absorbed on ancillary materials (e.g., mandrels, bagging, films, etc.) used in the manufacture of composites.

The Aerospace Corporation® alone has supported well over 50 failure investigations related to this failure mechanism covering a wide range of CE formulations. This issue not only affects the bulk of the composite but is also detrimental to the very outermost surfaces of the composite part and many times goes unidentified using typical laboratory type characterization techniques. Hydrolysis of the CE monomer occurring during cure tends to be highly localized near the moisture source and segregated to the very outer surface plies (e.g., ~2.0 mils). This makes the detection very difficult using conventional bulk characterization techniques. This degradation has also led to premature failures where composite adhesive bond strengths were only a fraction of expected values (20% of failure strength). Therefore, there remains a strong need to develop reliable quality control evaluation techniques to successfully pre-screen for issues related to this processing issue in CE-based composites.

In some embodiments, a nano-scale quality control technique (hereinafter referred to as "technique") is developed. The technique utilizes atomic force microscopy (AFM) to identify areas that have been contaminated or affected prior to costly tests and assembly campaigns. The technique may allow for an evaluation process using the composite cross-section to detect if any, and to what extent any, hydrolysis-affected regions exist. The technique also allows a quantification of the severity of the hydrolysis by evaluating the magnitude of the relative matrix material recession heights for any localized areas within the composite after a polishing procedure of the sample surface.

AFM imaging techniques that can be used include contact mode, non-contact mode, or intermittent contact (tapping) mode. In such an embodiment, the lateral scan range is adjusted to encompass multiple fibers for suitable averaging of fiber height measurements.

In order to analyze the affected area without having to perform a difficult sample preparation, which requires a physical separation of a very thin section, a small composite piece comprising of the entire laminate thickness is cross-sectioned and polished. This may be a sample preparation for microscopic image analysis. Subsequently, AFM topographic measurements are performed to evaluate the degree of matrix recession at various locations in the composite.

Polishing is a process that removes material and the softer matrix material is removed at a faster rate than the fiber in a composite part. The degree of matrix recession is determined by measuring the distance between the matrix and the fiber, which serves as a reference height. Any difference in the matrix recession in the hydrolysis-affected area versus unaffected area can therefore be quantitatively determined. For best result, both the test specimen (hydrolyzed) and the control specimen (non-hydrolyzed) are to be potted together and polished simultaneously.

CE resins cure through a cyclotrimerization reaction in which three —O—C≡N groups form a triazine ring. In the presence of moisture, the CE monomer reacts with water molecules instead of reacting with another monomer, thereby forming an imidocarbonic acid intermediate, which then rearranges into a carbamate structure. This carbamate structure may then inhibit the cyclo-trimerization reaction and reduce the density of triazine rings. This results in a polymer structure that is more linear and not as highly crosslinked, and therefore, results in lower mechanical and thermal properties. A higher degree of carbamate formation (hydrolysis of the monomer) may result in a less crosslinked polymer network, which would be expected to have a higher degree of recession when polished equivalently to a specimen with no degree of carbamate formation.

To evaluate the effectiveness of the AFM technique, a series of tests are performed to correlate the results of the AFM method with those of the standard DMA Tg method as well as to FWT strength tests. The concentration of moisture introduced during cure has been shown to be critical to the thermal degradation behavior and Tg of the TC410 resin. To simulate actual composite processing protocols more in line with manufacturing processes, an epoxy composite mandrel with increasing amount of out-time is used as the moisture source to manufacture and cure three separate, 8-ply unidirectional composites.

Additionally, a control sample is also cured identically utilizing a non-moisture absorbing, steel mandrel. Tg's by DMA are measured at both the mandrel side and tool side of each TC410 composite, since the mandrel is serving as the primary source with evidence from prior investigations that gradients may exist due to carbamate formation within the same composite. For these measurements, samples are carefully thinned down to 0.6 mm from either the bag side or the tool side outer surface.

Table 1 (see below) shows the measured Tg properties for the four conditions of composites manufactured.

TABLE 1

Glass Transition Temperatures (Tg) of Composite on Tool side and Bag side for Mandrels with increasing Moisture Content

| | Moisture level of mandrel | | | |
| --- | --- | --- | --- | --- |
| | Control (metal) | Low (LH) | Medium (MH) | High (HH) |
| Tool | 197° C. | 191° C. | 170° C. | 118° C. |
| Bag | 196° C. | 195° C. | 198° C. | 139° C. |
| delta | 1 | 4 | 31 | 21 |

As shown, the control specimen has an average Tg on both the mandrel and bag side of approximately 197° C. The low hydrolysis (LH) sample exhibits a Tg of 195° C. for the bag side and 191° C. for the tool side. This variation is expected since most of the absorbed moisture is typically on the surface of the mandrel and diffuses outward during cure, typically reacting with the plies most adjacent the tool. The same is observed for the composite specimen with medium hydrolysis (MH); however, the tool side Tg shows a significantly greater reduction than for the LH condition specimen. This variation is a result of the higher concentration of moisture diffusing from the mandrel. There is no significant change in the bag side Tg, since the hydrolysis remains quite localized based on the amount of moisture emanating from the mandrel. This localized behavior is consistent with the fact that the activation energy for hydrolysis is measured to be more favorable than that for the activation energy for cyclotrimerization.

For the specimen manufactured on the mandrel with the highest concentrations of moisture (HH), the mandrel side Tg further decreases to as low as 118° C. For this condition, the bag side Tg is shown to show a significant decrease when compared to the other bag-side segments. This is due to the larger concentration of moisture available to filter through the entire laminate resulting in a more hydrolysis of available cyanate functional groups leading to higher degree of carbamate formation through the entire cross-section. These Tg measurements confirm localized hydrolysis and carbamate formation as a result of moisture exposure during cure.

To observe the effect of localized hydrolysis on the matrix recession, cross-sections are taken of each of the composites followed by AFM measurements on the tool side and bag side of each specimen. The optical view 400 of each composite is shown FIG. 4, where all four samples (A)-(D) appear indistinguishable in terms of consolidation and porosity. Since AFM is a technique that enables nanometer-scale resolution topography analysis of a surface, any differences in wear or recession of the area after polishing could be correlated to a higher degree of carbamate formation compared to areas that had not. A higher degree of carbamate formation may result in a less crosslinked polymer network, which has a higher degree of recession when polished equivalently to a specimen with no degree of carbamate formation.

FIG. 2 shows an image 200(b) illustrating an example of the AFM surface topography scan as well as the line profile scan of the tool side for the control specimen, according to an embodiment of the present invention. From the picture shown in image 200(b) of FIG. 2, there appears to be a small variation between the average height at the top of the fiber versus the height of the surrounding matrix material, which appears somewhat recessed. Though there may be minimal degree of recession from the fiber itself after polishing, the fiber serves as a reference point to obtain a delta for each sample at a specific location (e.g., tool vs. bag side). In this case, the line profile verifies a change of approximately 50 nms.

Image 200(a) of FIG. 2, on the other hand, illustrates an AFM scan for the tool side of the High Hydrolysis (HH) specimen exhibiting a significant degree of recession, according to an embodiment of the present invention. In FIG. 2, image 200(a) shows the differential between the matrix and the fiber, which in this case is approximately 120 nm. This indicates that the specimen affected by carbamate formation wears at a significantly higher recession rate based on crosslink density.

Figure 3:
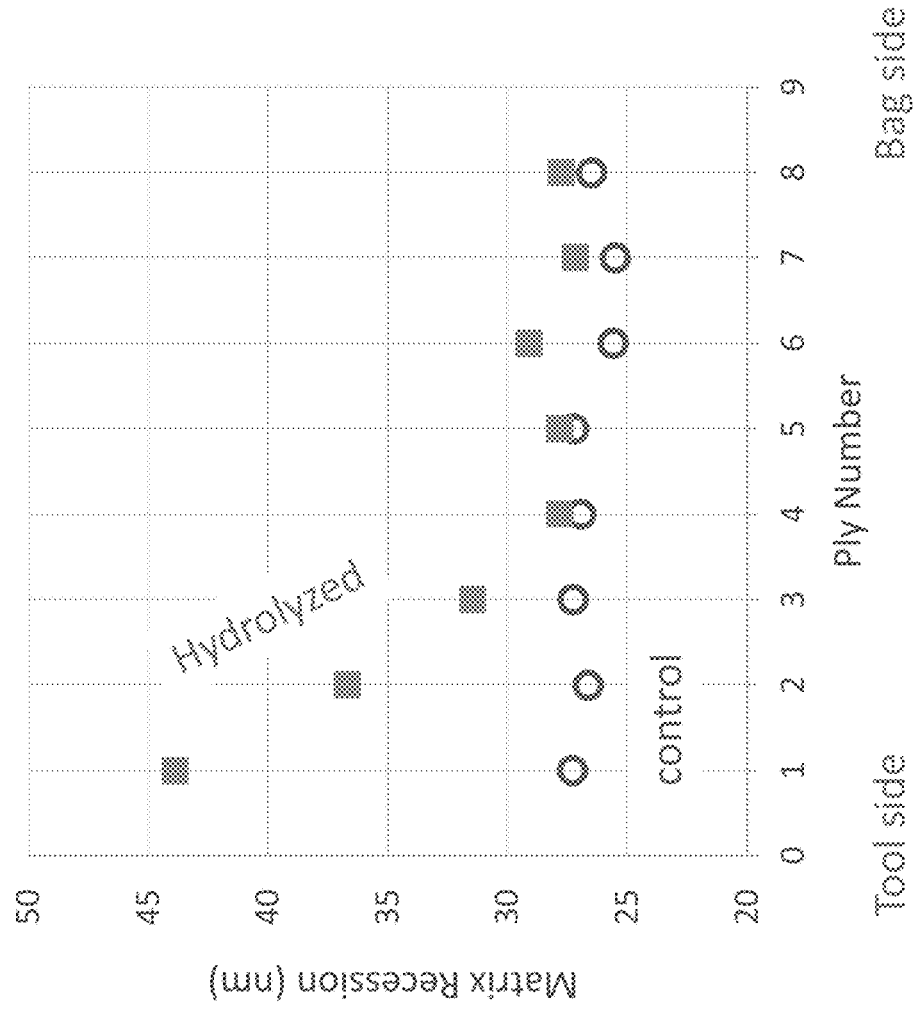
FIG. 3 is a graph illustrating a TC410 Matrix recession using AFM for each individual ply in the laminate for both the control and the hydrolyzed specimen according to an embodiment of the present invention.

FIG. 3 is a graph 300 illustrating a TC410 Matrix recession using AFM for each individual ply in the laminate for both the control and the hydrolyzed specimen according to an embodiment of the present invention. In graph 300, each data point shown in this plot shows a matrix degradation property of a single ply as opposed to the measurement shown in Table 1, where the measurements were done on multiple plies. A typical composite laminate includes multiple plies, and is virtually impossible to separate each individual ply from each other after manufacturing without causing damage. Therefore, by conventional measurement techniques, it is very difficult to evaluate the hydrolytic degradation properties of an individual ply. Using the technique described herein, it is easy to perform a ply-by-ply evaluation and determine exactly which plies have been degraded and the relative degree of the degradation for each ply.

Figure 5:
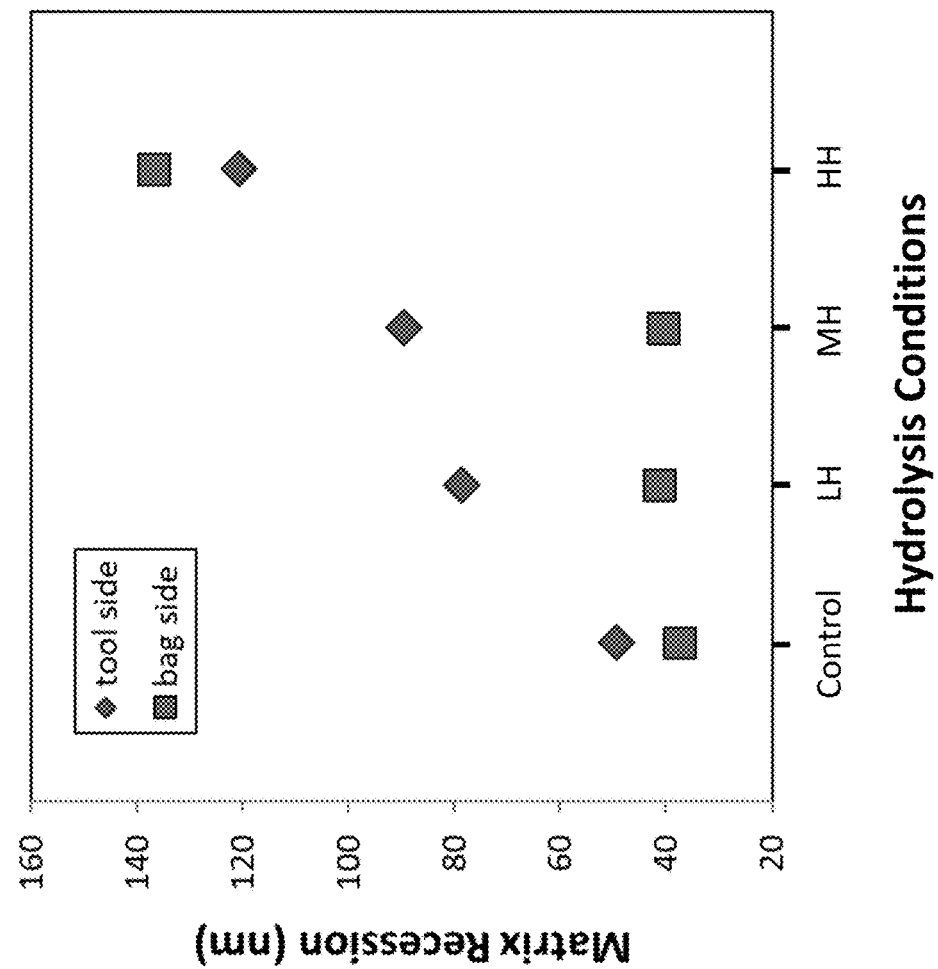
FIG. 5 is a graph illustrating a TC410 Matrix recession using AFM versus initial degree of hydrolysis for both tool side and bag side segments of 4 composite systems (control, LH, MH, HH), according to an embodiment of the present invention.

FIG. 5 is a graph 500 illustrating a summary chart for the relative recession rates for all the 4 composites (control, LH, MH, HH) investigated, according to an embodiment of the present invention. In graph 500, even though there is not any observable differences from the optical image analysis, there is a direct inverse relationship between the reported measured Tg of the segment (e.g. tool side) and the amount of recession rate experienced by the matrix material. All the bag side specimens except for the HH shows minimal recession, and the tool side specimens shows increasing amounts with increased carbamate formation (e.g., lower Tg). The only variation being the bag side versus tool side differences for the HH condition, which is due to higher variability in the material removal at such an extreme carbamate condition. The variability appears to increase with increasing hydrolysis and the overall extent of matrix recession as shown by the size of the error bars.

To see the effect of carbamate formation on the mechanical properties of TC410/M55J composites described in FIG. 5, the laminate specimens are bonded and mechanically tested to evaluate their matrix-dominated properties. Degradation due to carbamate formation is most readily observed when utilizing tests such as flatwise tension (FWT) to minimize any contributions from the fiber (FWT).

Figure 4:
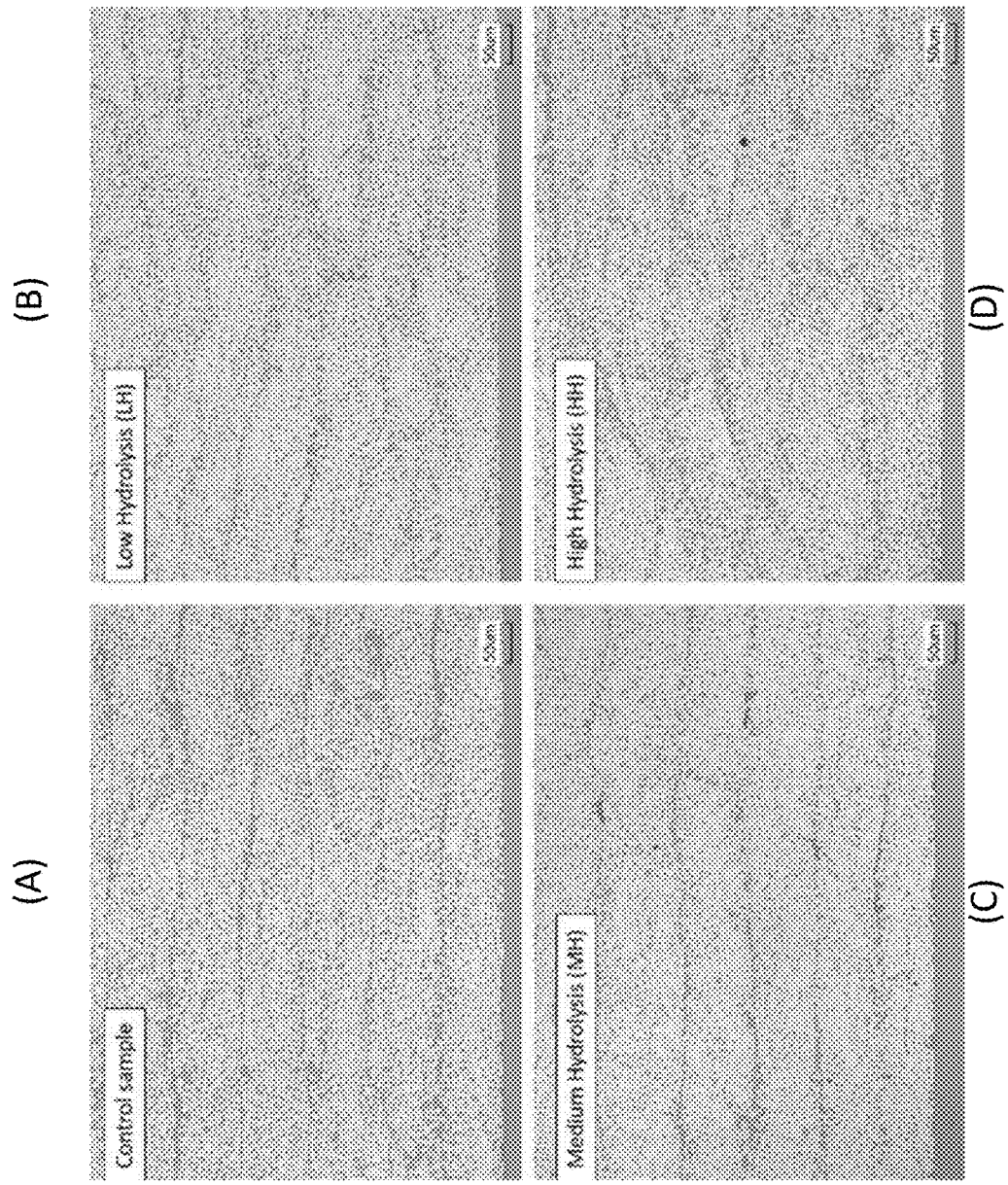
FIG. 4 is a cross-sectional image illustrating laminate of TC410/M55J manufactured on a control (a) metal mandrel versus a mandrel with increasing levels of moisture (b) low hydrolysis (c) medium hydrolysis (d) high hydrolysis, according to an embodiment of the present invention.

FIG. 6 is a graph 600 illustrating a summary of the average FWT strength versus the matrix recession (i.e., fiber height by AFM) on the mandrel side (tool side) of the composite. The mandrel side was chosen since all of the failures occurred on the mandrel side of the composite except for that of the control specimens. The control composites manufactured on a metal mandrel would not be expected to be affected by hydrolysis. As shown, the measured FWT strength decreases with increasing matrix recession since the material would be expected to be weaker with increased hydrolysis. The FWT trend appears linear versus the matrix recession with a slope of approximately −0.16 MPa/nm over the selected tested range. As shown in FIG. 4, there does not appear to be any disparity in porosity utilizing image analysis between the different samples with increased carbamate formation. Therefore, any FWT strength degradation is believed to be primarily due to changes in the physical behavior of the resin related to decreases in cross-linking density of the network, which is also manifested as increased matrix recession by AFM measurement followed by cross-sectional polishing. The higher recession rates observed in the carbamate-affected areas are a direct indication of the matrix degradation and is clearly shown to correlate well with the FWT strength degradation. The AFM technique is shown be an excellent alternate QC method when the standard DMA analysis is not feasible.

FIG. 7 is a diagram illustrating a cross-section analysis 700 of a composite laminate, according to an embodiment of the present invention. In this embodiment, a small piece of a deposit taken from a composite laminate 705 is inserted into an epoxy mounting for cross-sectional analysis. Prior to this, the composite laminate 705 was cured against mandrel 710. In one example, a typical specimen would be the size of a thumb nail. The composite laminate includes a plurality of plies that are cured simultaneously as the constituent of the laminate. Because each ply is extremely thin (e.g., on the order of ~1 mil), a cross-sectional polishing is performed. For example, polishing for cross-sectional analysis may be performed by optical or scanning electron microscopy. For example, a cross-sectional sample may be ground flat using a large grit sandpaper (e.g., ~200 grit). Then, using gradually fine grits (e.g., 600 grit→800 grit→1000 grit→1200 grit, etc.). The final polish could be done using polishing pastes with finer particles (e.g., 0.5 μm or 0.25 μm diamond paste) for "mirror-like" finish.

In some embodiments, a technique, such as AFM, with a nanometer resolution imaging is used to study each ply. See element 725. This technique may find a compromised ply. In FIG. 7, a deposit 715 from the composite laminate (the black line) 705 comprises of multiple plies. In FIG. 7, cross-sectional optical image 725 shows a collection of white dots, which are individual carbon fibers coming out of the screen and running perpendicular to the screen. FIG. 7 also shows dark lines 725 going across laterally, indicates the interface between plies where the plies come together. In image 700, there are 5 plies in the optical view shown. Element 720 in this embodiment is a cross-section puck that includes deposits 715 from composite laminate 705. Put simply, element 720 is the sample specimen, which is grinded and polished, and is prepared for cross-sectional analysis.

This technique allows for evaluating one ply at a time as demonstrated in FIG. 3 without separating the plies. This is better than the conventional method where one (i.e., a scientist) has to separate each ply physically to do the analysis. With this technique, there is no destruction of the plies while allowing for evaluating one ply at a time. The destruction refers to the ply of interest for the purpose of the evaluation of the matrix material. A physical separation either by peeling or sanding could damage the ply to the point of compromising the analysis by conventional evaluation technique. If the plies are not separated, then one only has to perform the evaluation of multiple plies, which would result in average effect over multiple plies, resulting in a potentially false negative result. With this new technique, a clear evaluation of each individual ply is easily performed without the loss of the data quality either due to averaging or damaging.

In FIG. 7, image 730 shows a matrix recession comprising of a plurality of fibers and matrix resins. The matrix resin hold the fiber together. This is critical to the strength of the overall composite laminate.

It should be noted that conventional methods consist of evaluating the entire thickness of the composite laminate, which can give a false negative. For example, if a composite laminate has one or two plies that are affected, the convention methods may give a false negative because the entire thickness is evaluated rather than evaluating each individual ply. Thus, the conventional techniques lacks precise spatial precision. By using the techniques, as described herein, a localized failure may be detected.

FIG. 8 is a flow diagram 800 illustrating a quality control evaluation method of a CE matrix resin material within a CFRP composite concerning localized hydrolytic degradation, according to an embodiment of the present invention. First, assemble the sample preparation, i.e., take small pieces of the composite laminate, and then polishing the small pieces. Next, after sample preparation is completed, the small pieces are placed under an atomic force microscope to see more details in terms of matrix material removal.

In some embodiments, method 800 includes inserting a small piece of a deposit extracted from a composite laminate into an epoxy for cross-sectional analysis at 805. At 810, method 800 include performing cross-sectional polishing on the small piece of the deposit. At 815, method 815 includes performing nano-scale resolution three dimensional image analysis to study a plurality of plies in the small piece of the deposit to evaluate each ply in the plurality of plies without destruction of each ply.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A process for evaluating quality of cyanate ester matrix resin material, comprising:
   inserting a small piece of a deposit extracted from a composite laminate into an epoxy for cross-sectional analysis;
   performing cross-sectional polishing on the small piece of the deposit; and
   performing nanometer-scale resolution three dimensional imaging to study a plurality of plies in the small piece of the deposit to evaluate each ply without separating the plurality of plies.

2. The process of claim 1, further comprising:
   extracting the small piece of the deposit from the composite laminate.

3. The process of claim 1, wherein the composite laminate comprises the plurality of lies, with each of the plurality of plies that are cured simultaneously as the constituent of the composite laminate.

4. The process of claim 1, wherein the performing of the cross-sectional polishing comprises
   cross-sectioning the small piece of the deposit; and
   performing polishing on the small piece of the deposit using a polishing method suitable for doing optical or scanning electron microscopy.

5. The process of claim 4, wherein the performing of the polishing comprises
   applying a plurality of pastes with finer particles to create a "mirror-like" finish.

6. The process of claim 5, wherein the finer particles comprise a 0.5 µm or 0.25 µm diamond paste.

7. The process of claim 1, wherein the performing of the nanometer-scale resolution three dimensional imaging identifies a compromised ply in one of the plurality of plies.

8. A process for evaluating quality of cyanate ester matrix resin material, comprising:
   curing a composite laminate against a mandrel;
   inserting a small piece of a deposit extracted from the composite laminate into an epoxy for cross-sectional analysis;
   performing cross-sectional polishing on the small piece of the deposit; and
   performing nanometer-scale resolution three dimensional imaging to study a plurality of plies in the small piece of the deposit to evaluate each ply without separating the plurality of plies.

9. The process of claim 8, further comprising:
   extracting the small piece of the deposit from the composite laminate.

10. The process of claim 8, wherein the composite laminate comprises the plurality of lies, with each of the plurality of plies that are cured simultaneously as the constituent of the composite laminate.

11. The process of claim 8, wherein the performing of the cross-sectional polishing comprises
    cross-sectioning the small piece of the deposit; and
    performing polishing on the small piece of the deposit using a polishing method suitable for doing optical or scanning electron microscopy.

12. The process of claim 11, wherein the performing of the polishing comprises
    applying a plurality of pastes with finer particles to create a "mirror-like" finish.

13. The process of claim 12, wherein the finer particles comprise a 0.5 µm or 0.25 µm diamond paste.

14. The process of claim 8, wherein the performing of the nanometer-scale resolution three dimensional imaging identifies a compromised ply in one of the plurality of plies.

15. A process for evaluating quality of cyanate ester matrix resin material, comprising:
    curing a composite laminate against a mandrel;
    inserting a small piece of a deposit extracted from the composite laminate into an epoxy for cross-sectional analysis;
    performing cross-sectional polishing on the small piece of the deposit; and
    performing nanometer-scale resolution three dimensional imaging to study a plurality of plies in the small piece of the deposit to evaluate each ply without separating the plurality of plies, wherein
    the performing of the nanometer-scale resolution three dimensional imaging comprising identifying one or more compromised plies in one of the plurality of plies.

16. The process of claim 15, further comprising:
    extracting the small piece of the deposit from the composite laminate.

17. The process of claim 15, wherein the composite laminate comprises the plurality of lies, with each of the plurality of plies that are cured simultaneously as the constituent of the composite laminate.

18. The process of claim 15, wherein the performing of the cross-sectional polishing comprises
    cross-sectioning the small piece of the deposit; and
    performing polishing on the small piece of the deposit using a polishing method suitable for doing optical or scanning electron microscopy.

19. The process of claim 18, wherein the performing of the polishing comprises
    applying a plurality of pastes with finer particles to create a "mirror-like" finish.

20. The process of claim 19, wherein the finer particles comprise a 0.5 µm or 0.25 µm diamond paste.

* * * * *